US009398884B2

(12) United States Patent  
Tanishima et al.

(10) Patent No.: US 9,398,884 B2  
(45) Date of Patent: Jul. 26, 2016

(54) BIOLOGICAL INFORMATION MONITORING APPARATUS AND ALARM CONTROL METHOD

(75) Inventors: Masami Tanishima, Tokyo (JP); Masahiro Echigo, Tokyo (JP); Rie Oyagi, Tokyo (JP); Shinji Tezuka, Tokyo (JP); Yoshinori Enomoto, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 421 days.

(21) Appl. No.: 12/899,684

(22) Filed: Oct. 7, 2010

(65) Prior Publication Data

US 2011/0080294 A1 Apr. 7, 2011

(30) Foreign Application Priority Data

Oct. 7, 2009 (JP) ................................. 2009-233153

(51) Int. Cl.
*G08B 23/00* (2006.01)
*A61B 5/00* (2006.01)
*A61B 5/1455* (2006.01)

(52) U.S. Cl.
CPC .............. *A61B 5/746* (2013.01); *A61B 5/1455* (2013.01); *A61B 2560/0276* (2013.01)

(58) Field of Classification Search
CPC .... A61B 5/746; A61B 5/0205; A61B 5/7271; A61B 5/7275; A61B 5/7475; A61B 5/1455; G06F 19/345; G06F 19/3406; G06F 19/3412
USPC ................................ 340/573.1; 600/300, 301
See application file for complete search history.

(56) References Cited

U.S. PATENT DOCUMENTS

| 5,786,755 | A | 7/1998 | Cicchino et al. |
| 5,865,736 | A | 2/1999 | Baker et al. |
| 6,560,471 | B1 | 5/2003 | Heller et al. |
| 7,022,072 | B2 * | 4/2006 | Fox et al. ..................... 600/300 |
| 2003/0125612 | A1 | 7/2003 | Fox et al. |
| 2004/0263337 | A1 | 12/2004 | Tarauchi et al. |
| 2006/0220881 | A1 * | 10/2006 | Al-Ali et al. ............... 340/573.1 |
| 2007/0106126 | A1 * | 5/2007 | Mannheimer et al. ..... 340/573.1 |
| 2008/0094227 | A1 | 4/2008 | Becker et al. |
| 2009/0221887 | A1 | 9/2009 | Mannheimer |

(Continued)

FOREIGN PATENT DOCUMENTS

| CN | 1575745 A | 2/2005 |
| JP | 5-7623 A | 1/1993 |

(Continued)

OTHER PUBLICATIONS

Extended European Search Report, Feb. 3, 2011.

(Continued)

*Primary Examiner* — Thomas Mullen
(74) *Attorney, Agent, or Firm* — Kenealy Vaidya LLP (57) ABSTRACT

A biological information monitoring apparatus operable to measure biological information of a patient by detecting a biological signal of the patient, and operable to output an alarm, includes an alarm controller which changes the alarm. The alarm includes a first alarm of a first priority and a second alarm of a second priority. When a first condition is satisfied, the first alarm is output. When a second condition is satisfied after the first alarm is output, the alarm controller changes from the first alarm to the second alarm to be output.

22 Claims, 4 Drawing Sheets

(56) References Cited

U.S. PATENT DOCUMENTS

2009/0247848 A1* 10/2009 Baker, Jr. .................. 340/573.1
2009/0247851 A1    10/2009 Batchelder
2012/0232359 A1     9/2012 Al-Ali et al.

FOREIGN PATENT DOCUMENTS

| JP | 2000-201900 A | 7/2000 |
| --- | --- | --- |
| JP | 2002-282213 A | 10/2002 |
| JP | 2003-235813 A | 8/2003 |
| JP | 2004-5341 A | 1/2004 |
| JP | 2008-501426 A | 1/2008 |
| JP | 2008-62072 A | 3/2008 |
| JP | 2008-535540 A | 9/2008 |
| JP | 2009-39357 A | 2/2009 |
| JP | 2009-510631 A | 3/2009 |
| JP | 2009-101214 A | 5/2009 |

OTHER PUBLICATIONS

Japanese Office Action for the related Japanese Patent Application No. 2009-233153 dated Apr. 25, 2013.
Chinese Office Action for the related Chinese Patent Application No. 201010511708.5 dated Nov. 26, 2013.
Japanese Office Action for the related Japanese Patent Application No. 2009-233153 dated Feb. 26, 2014.
Decision to Dismiss an Amendment for Japanese Patent App. No. 2009-233153 (Oct. 23, 2014) with English translation thereof.
Report of Reconsideration by Examiner before Appeal for Japanese Patent App. No. 2009-233153 (Apr. 17, 2015) with English translation thereof.
Japanese Office Action for the related Japanese Patent App. No. 2009-233153 (Dec. 22, 2015) with English translation thereof.

\* cited by examiner

BIOLOGICAL INFORMATION MONITORING APPARATUS AND ALARM CONTROL METHOD

BACKGROUND OF THE INVENTION

The present invention relates to a biological information monitoring apparatus which displays biological information that is obtained by processing a detection signal detected from a living body, on a displaying unit, which generates an alarm sound through a speaker, or which lights an alarm lamp in an alarm indicator configured by LEDs and the like, and particularly to a biological information monitoring apparatus which can output a visual alarm and auditory alarm in which the alarm priority of a vital alarm that is to be output when there is an abnormality of the detected signal, or that of a technical alarm that is to be output when there is an abnormality of the biological information monitoring apparatus, a sensor, or the measurement environment is changed depending on the situation. The invention relates also to an alarm control method.

As an example of a patient monitoring apparatus, the following configuration is disclosed in JP-A-2009-101214.

A typical pulse oximeter measures two biological parameters (the present oxygen saturation (hereinafter, often abbreviated as sat) of blood hemoglobin, and the pulse rate (hereinafter, often referred to as rate)). For alarm purposes, normal ranges which are preferably maintained in the patient are determined, and low and high thresholds are set for both the sat and the rate. In the case of a neonatal infant, for example, the sat is preferably maintained between 80 and 95 percent, and the rate is preferably maintained in the range of 90 to 190 beats/minute.

From the two measured parameters, four alarm types (low sat, high sat, low rate, and high rate) are produced. In a typical pulse oximeter, when one of the sat and the rate goes outside the normal range, an alarm is immediately output, and, when both the sat and the rate return within the normal range, the alarm is immediately ended. Typically, an alarm is in the form of an auditory sound and/or visual indicator.

Each occurrence in which a measured parameter goes outside the normal range is referred to as an event. In a typical pulse oximeter, namely, each event corresponds to an alarm, and the time duration of the alarm coincides with the time duration of the event.

Usually, many alarms generated by a typical pulse oximeter are not considered so as to correspond to events which are clinical effective.

The definition of clinical effectiveness varies depending on the patient and the environment. Usually, it is related to the severity and time duration of the event of interest. For example, a very shallow desaturation is considered effective only when sustained for a relatively long time duration.

Similarly, a desaturation of a very short duration is considered effective only when it falls very deep below the low sat threshold. Moreover, a parameter measurement error due to noise or signal artifact produces a false event. Any alarm which corresponds to a clinically effective event is considered a nuisance alarm.

Studies which attempt to reduce the number of saturation alarms have been announced. These studies are directed to lowering of the alarm threshold or waiting of a certain fixed time duration after the threshold is passed.

Lowering of the alarm threshold is problematic because the oxygen saturation of the patient indefinitely remains below the original threshold (which is higher than the new threshold), and an alarm is not produced.

Delaying of the production of an alarm by a fixed time period is also problematic because of a potentially serious situation in which the oxygen saturation of the patient abruptly falls to or remains at a very low level at which prompt medical treatment is required.

Therefore, the disclosed subject matter provides a method and apparatus for controlling an alarm in a medical diagnostic apparatus in which an alarm is produced when a measured value of a biological parameter passes a threshold.

In the disclosed subject matter, both the time amount for which the measured value passes the threshold, and the amount by which the measured value passes the threshold are determined or quantized). An alarm is inhibited based on a combination of the time amount and the amount by which the threshold is passed. Preferably, the combination is an integral or some integral functions.

In a preferred embodiment, for a saturation alarm of a pulse oximeter, the integral of the amount by which the oxygen saturation exceeds an upper threshold or falls below a lower threshold is calculated. When the integral exceeds a predetermined value, the saturation alarm is produced.

For a rate alarm of a pulse oximeter, similarly, the preferred embodiment calculates the integral of the amount by which the pulse rate exceeds upper and lower thresholds. When the integral exceeds a predetermined value, the rate alarm is produced.

As an alarm standard for a biological information apparatus (medical electrical equipment ("ME") apparatus), international IEC 60601-1-8 is set. A summary of the standard will be described.

Table 1 shows alarm condition priorities in the standard of IEC 60601-1-8.

It is assumed that alarm conditions are assigned to one or more of a high priority, a medium priority, and a low priority. The priority is determined based on the risk management process (ISO 14971) shown in Table 1. The alarm condition priorities must be shown in an operation manual, and the priorities may be identified in a group.

Table 2 shows visual alarm signals in the standard of IEC 60601-1-8.

In the case where an alarm indicator is necessary for the operator to identify an apparatus or part of the apparatus which requires a response or awareness by the operator, characteristics such as shown in Table 2 are provided.

Tables 3(a) and 3(b) show alarm sounds (auditory alarms) in the standard of IEC 60601-1-8.

Table 4 shows melody alarms in auditory alarms in the standard of IEC 60601-1-8.

An alarm system which emits an alarm sound must have at least one of the following sets (1) and (2):

(1) the priority is patterned, and adapted to Tables 3(a) and 3(b); and (2) the alarm is generated by a different technique (such as an audio alarm signal), and the adequacy thereof is confirmed.

In Table 4, when the absolute frequency of [c] is between 150 to 500 Hz, sound can be produced by a different key. For auditory alarm signals of all alarm systems, "normal" burst can be used. In Table 4, c, d, e, f, g, a, b, and C are musical relative pitches, and C is higher than c by one octave. An alarm signal of the high priority is generated by the five indicated pulses, and repeated once so that a total of ten pulses are obtained.

TABLE 1

Alarm condition priority

| Potential result when fail to respond to cause of alarm state | Generation of potential injury | | |
|---|---|---|---|
| | Immediate | Rapid | Late |
| Death or irreversible injury | High priority (H) | High priority (H) | Medium priority (M) |
| Reversible injury | High priority (H) | Medium priority (M) | Low priority (L) |
| Minor injury or unpleasant feeling | Medium priority (M) | Low priority (L) | Low priority (L) or non-alarming signal |

TABLE 2

Characteristics of light of alarm indicator

| Class of alarm | Color of indicator light | Blink frequency | Operation period |
|---|---|---|---|
| High priority (H) | Red | 1.4 to 2.8 Hz | 20 to 60% are in lit state |
| Medium priority (M) | Yellow | 0.4 to 0.8 Hz | 20 to 60% are in lit state |
| Low priority (L) | Cyan or yellow | Constant (lit state) | 100% are in lit state |

TABLE 3(b)

Burst characteristics of auditory alarm signal

| Characteristics | Alarm signal of high priority | Alarm signal of medium priority | Alarm signal of low priority |
|---|---|---|---|
| Pulse number of burst | 10 | 3 | 1 or 2 |
| Spacing between pulses (ts) (see FIG. 2) | | | |
| Between 1st pulse and 2nd pulse | x | y | y |
| Between 2nd pulse and 3rd pulse | x | y | N/A |
| Between 3rd pulse and 4th pulse | 2x + ts | N/A | N/A |
| Between 4th pulse and 5th pulse | x | N/A | N/A |
| Between 5th pulse and 6th pulse | 0.35 to 1.30 s | N/A | N/A |
| Between 6th pulse and 7th pulse | x | N/A | N/A |
| Between 7th pulse and 8th pulse | x | N/A | N/A |
| Between 8th pulse and 9th pulse | 2x + ts | N/A | N/A |
| Between 9th pulse and 10th pulse | x | N/A | N/A |
| Time between bursts | 2.5 to 15.0 s | 2.5 to 30.0 s | >15 s or not repeated |
| Amplitude difference between two arbitrary pulses | Maximum 10 dB | Maximum 10 dB | Maximum 10 dB |

TABLE 4

Melody alarm

| Cause | Medium priority | High priority |
|---|---|---|
| General | ccc | ccc-cc |
| Heart | ceg | ceg-gC |
| Artificial perfusion | cf#c | cf#c-cf# |
| Ventilation | caf | caf-af |
| Oxygen | Cba | Cba-gf |
| Temperature/energy supply | cde | cde-fg |
| Supply of medicine or liquid | Cdg | Cdg-Cd |
| Failure of apparatus or supplied product | Ccc | Ccc-Cc |

As described above, the high priority, medium priority, and low priority which are alarm condition priorities in the alarm standard for a biological information apparatus (ME apparatus) are defined in detail based on the risk management process (ISO 14971) shown in Table 1, and visual and auditory alarms which are output forms of the priorities are determined in accordance with the alarm priorities.

An example of a biological information monitoring apparatus which announces an alarm by means of an auditory sound and/or visual indicator will be described with reference to FIG. 1.

Figure 1:
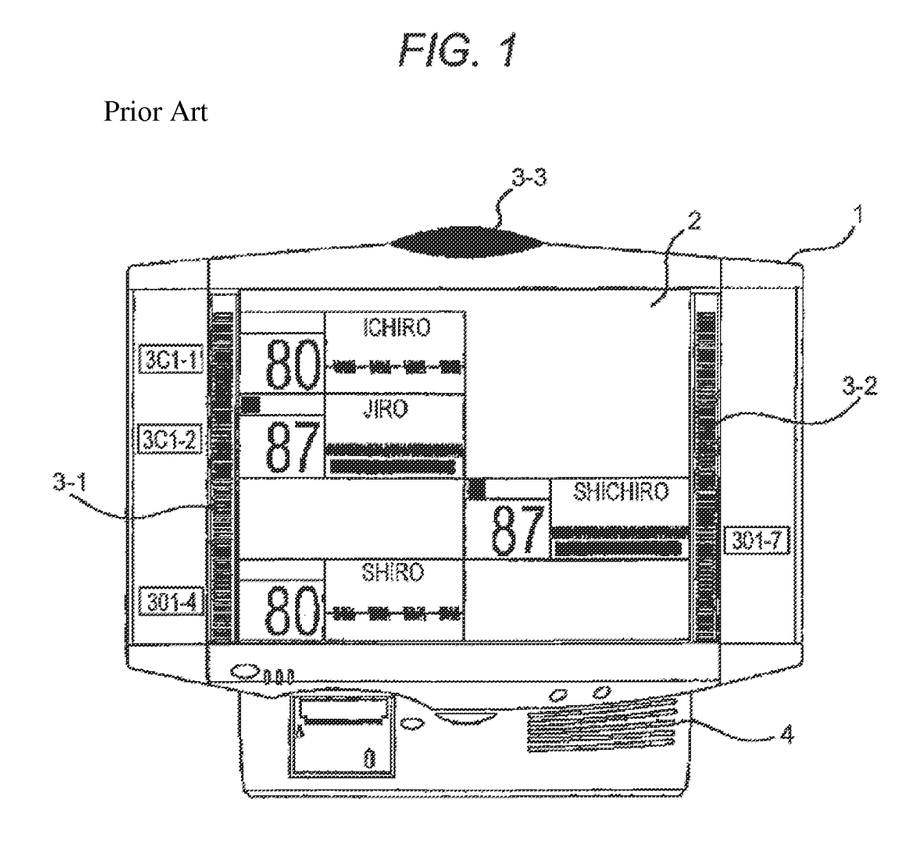
FIG. 1 is a view showing the appearance of a biological information monitoring apparatus of the station type which is placed in a nurse's station or the like, and in which biological signals of a plurality of patients can be simultaneously monitored.

FIG. 1 is an external view of a biological information monitoring apparatus of the station type which is placed in a nurse's station or the like, and in which biological signals of a plurality of patients can be simultaneously monitored.

In FIG. 1, 1 denotes the biological information monitor of the station type, and 2 denotes a display screen on which numerals and waveforms that are obtained as a result of processing biological signals of a plurality (in the illustrated apparatus, eight) of patients are simultaneously displayed (in the illustrated state, only four patients are monitored).

The reference numerals 3-1, 3-2, and 3-3 denote display output portions for a visual alarm. The display output portions 3-1, 3-2 are individual display portions which can perform displays respectively corresponding to individual patients, and the display output portion 3-3 is a common display portion which is common to all patients. Each of the display portions is configured by, for example, LEDs, and selectively displays red, yellow, cyan light, or like alarm light in accordance with the alarm priority. In the display screen 2, furthermore, a visual alarm may be displayed in the display regions respectively corresponding to individual patients.

The reference numeral 4 is a speaker which outputs an auditory alarm. The speaker can output an alarm corresponding to the alarm priority by means of different frequencies, duration times, and the like.

In the above-described pulse oximeter, for a saturation alarm, the integral of the amount by which the oxygen saturation exceeds the upper threshold or falls below the lower threshold is calculated. When the integral exceeds the predetermined value, the saturation alarm is produced.

Until the saturation alarm is produced, therefore, the exceeding (falling) amount is integrated. Therefore, an influence due to noise or signal artifact is eliminated. When the saturation alarm is once produced, however, the saturation alarm is not cancelled unless the oxygen saturation returns to the upper threshold or lower, or to the lower threshold or higher.

In such a state where, after the saturation alarm is once produced, the oxygen saturation remains stagnant in the vicinity of the upper or lower threshold, the saturation alarm is not cancelled, and the alarm announcement in the constant audio and/or visual form is continued, so that there arises a possibility that the observer becomes accustomed to the alarm and overlooks a serious abnormality.

In the integration, in the case where, because of an unexpected phenomenon or the like, the oxygen saturation largely falls below the low sat threshold in a very short time and the saturation alarm is once produced, even when the phenomenon is improved and the oxygen saturation returns to the vicinity of the threshold, the priority is maintained.

In this case, although an alarm which has a low priority is originally generated, an emergency alarm is output, thereby causing a possibility that such an alarm interferes with the work of a medical person.

In the alarm standard for a biological information apparatus (ME apparatus), as described above, the high priority, the medium priority, and the low priority are visual and auditory alarms which are defined in detail based on the risk management process (ISO 14971) shown in Table 1. Consequently, there is a problem in that, in the case where a visual or auditory alarm (particularly, the low priority or the medium priority) is continued, it can become overlooked if it becomes prolonged.

Specifically, in a state where the oxygen saturation stagnates in the vicinity of the upper or lower threshold (the medium priority), the same priority is maintained, and hence the alarm announcement in the constant audio and/or visual form is continued as indicated in above-described Tables 1 to 4. Consequently, there is a possibility that a serious abnormality is overlooked because of accustomed recognition of the observer that the priority remains unchanged.

A generation of a technical alarm means that a failure of a biological signal measuring apparatus itself, a state where checking of a probe or detection of a pulse wave is disabled, or the like occurs. However, this is not directly related to a phenomenon in which an abnormality is caused in the biological signal of the patient. Even when a technical alarm is generated by an operation of a body motion of the patient such as separation of an electrode or a probe, it is often the case that restoration is immediately performed. Therefore, there is a possibility that the alarm is overlooked with a sense of expectance of recovery.

SUMMARY

It is therefore an object of the invention to provide a biological information monitoring apparatus having a function of changing an alarm priority in which, in the case where, after a vital alarm that is output in response to an abnormality of a biological signal, or a technical alarm that is output in response to an abnormality of the biological information monitoring apparatus, a sensor, or the measurement environment, the alarm is continued at the same priority, the priority of the alarm can be changed (for example, from the medium priority to the high priority) when the alarm state satisfies predetermined conditions.

Examples of the abnormality of the measurement environment are a state where, when a transmitter wirelessly transmits a measured biological signal, the biological information monitoring apparatus which is scheduled to receive the signal cannot receive the biological signal because of an interruption of the radio wave or a failure of reception, and a phenomenon in which the contact impedance of an electrode is increased and noises enter the signal.

In order to achieve the object, according to the invention, there is provided a biological information monitoring apparatus operable to measure biological information of a patient by detecting a biological signal of the patient, and operable to output an alarm, the biological information monitoring apparatus comprising: an alarm controller which changes the alarm, wherein the alarm includes a first alarm of a first priority and a second alarm of a second priority, wherein when a first condition is satisfied, the first alarm is output, and when a second condition is satisfied after the first alarm is output, the alarm controller changes from the first alarm to the second alarm to be output.

The alarm including the first alarm and the second alarm may be a technical alarm which is output when the biological information monitoring apparatus, a sensor for measuring the biological information, or measurement environment is abnormal. The second condition may be a condition that an abnormal state in which the biological information monitoring apparatus, the sensor, or the measurement environment is abnormal is continued for a time period.

The alarm including the first alarm and the second alarm may be a vital alarm which is output when the detected biological signal is abnormal. The second condition may be at least one of a condition that an abnormal state in which the detected biological signal is abnormal is continued for a time period and a condition that the detected biological signal passes a threshold indicating a dangerous state.

The biological information monitoring apparatus may further include: an inputting unit. After the alarm controller changes from the first alarm to the second alarm, a user may operate the inputting unit to change from the second alarm to the first alarm to be output.

The alarm including the first alarm and the second alarm may be a vital alarm which is output when the detected biological signal is abnormal. In a case where, after the alarm controller changes from the first alarm to the second alarm, the detected biological signal passes a threshold to an area indicating a dangerous state, and the detected biological signal returns from the area and passes the threshold, the alarm controller may change from the second alarm to the first alarm to be output.

The first condition may be a condition that the detected biological signal passes a threshold, and the threshold of the second condition may be set or interlocked with the setting of the threshold of the first condition.

Each of the time period and the threshold may be set from a plurality of candidate values.

The alarm including the first alarm and the second alarm may include at least one of a visual alarm and an auditory alarm. In the visual alarm, a blinking rate in the second alarm may be set higher than a blinking rate in the first alarm, and, in the auditory alarm, a volume in the second alarm may be set higher than a volume in the first alarm.

The alarm including the first alarm and the second alarm may include at least one of a visual alarm and an auditory alarm. In the visual alarm, a blinking rate in the second alarm may be set lower than a blinking rate in the first alarm, and, in the auditory alarm, a volume in the second alarm may be set lower than a volume in the first alarm.

The alarm including the first alarm and the second alarm may include at least one of a visual alarm and an auditory alarm. In the visual alarm, a display color of the first alarm may be different from a display color of the second alarm, and, in the auditory alarm, a sound of the first alarm may be different from a sound of the second alarm.

The alarm may be a technical alarm which is output when the biological information monitoring apparatus, a sensor for measuring the biological information that includes at least one of an oxygen saturation, a blood pressure, an electrocardiogram, and respiration, or an interface between the sensor and the patient is abnormal, or a reception of a wireless signal is failed.

The second priority may be higher in priority than the first priority.

The first priority may be higher in priority than the second priority.

In order to achieve the object, according to the invention, there is also provided an alarm control method comprising: outputting a first alarm of a first priority when a first condition is satisfied, and when a second condition is satisfied after outputting the first alarm, changing from the first alarm to a second alarm of a second priority to be output.

DETAILED DESCRIPTION OF EMBODIMENTS

The configuration of the invention will be described with reference to FIG. 2.

Figure 2:
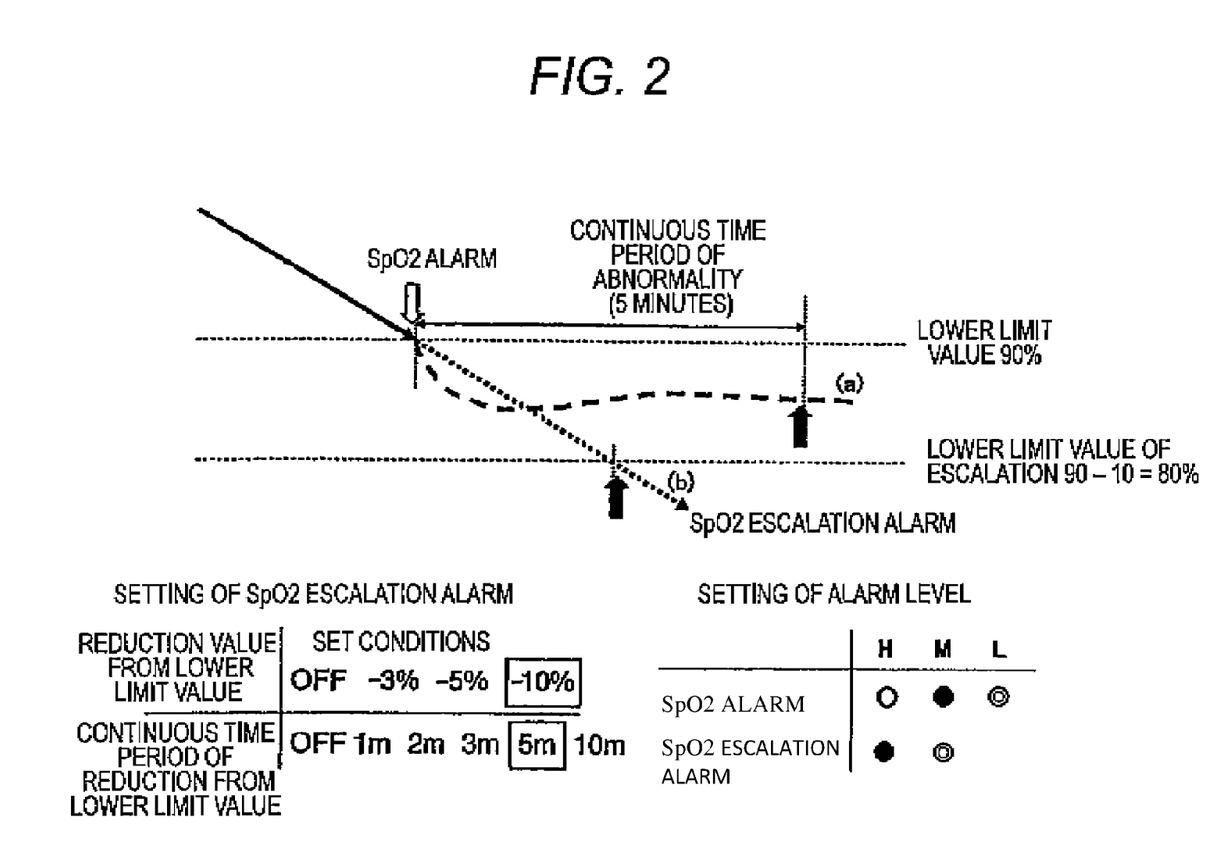
FIG. 2 is a view illustrating an example of an alarm priority change in the invention in the case where the state of the alarm satisfies predetermined conditions, by using an example of a measurement of the oxygen saturation (SpO2).

FIG. 2 illustrates an example of an alarm priority change, by an alarm controller of a biological information monitoring apparatus in the invention, in which the priority of an alarm is changed (the alarm is changed) in the case where the state of the alarm satisfies predetermined conditions, by using an example of a measurement of the oxygen saturation (SpO2).

FIG. 2 shows the case where a measured value of the SpO2 is reduced by falling below 90% which is a preset lower limit value.

In FIG. 2, the priority change of the SpO2 alarm is set in the following manner. As illustrated, as the reduction value (the threshold at which an abnormal state advances, and which indicates a dangerous state) from the lower limit value, −10% is set among OFF, −3%, −5%, and −10%, and, as the continuous time period of the reduction from the lower limit value, 5 m (minutes) is set among OFF, 1 m (minute), 2 m (minutes), 3 m (minutes), 5 m (minutes), and 10 m (minutes).

Each of the settings of the continuous time period and the reduction value from the lower limit value can be selected from a plurality of values.

The reduction value from the lower limit value can be set as a rate (%) or a fixed value (in the example, −10%), and may be automatically changed in an interlocked manner with the setting of the lower limit value. When the setting is changed in an interlocked manner, a change of the alarm priority can be automatically set while a medical person is not particularly conscious of minor settings.

The alarm levels (priorities) are set in the following manner. The normal SpO2 alarm is set to M level among H, M, and L levels, and the SpO2 alarm after the priority is changed is set to H level among H and M levels.

When, in this state, the measured value of the SpO2 is reduced and falls below 90% which is the lower limit value, the normal SpO2 alarm is generated, and the alarm of the medium priority configured by a visual alarm (yellow indicator display) and an auditory alarm (pulses of 150 to 1,000 Hz, and the duration time of 125 to 250 ms) is generated.

In the invention, as described above, the priority change of the SpO2 is set so that, as illustrated, −10% is set as the reduction value from the lower limit value, among OFF, −3%, −5%, and −10%, and 5 m (minutes) is set as the continuous time period of the reduction from the lower limit value, among OFF, 1 m (minute), 2 m (minutes), 3 m (minutes) 5 m (minutes), and 10 m (minutes). In the case where, even when the measured value of the SpO2 is reduced by falling below 90% which is the lower limit value, this state exceeds five minutes which is the set value of the continuous time period of the SpO2 alarm, the measured value of the SpO2 is not increased above the lower limit as shown by (a) in FIG. 2, the priority is escalated (changed), and the alarm level is switched to the alarm of the high priority.

Also in the case where, as shown by (b) in FIG. 2, the measured value of the SpO2 is further reduced by falling below 90% which is the lower limit value to exceed 10% which is the reduction value from the lower limit value (90−10=80%: a lower limit value of escalation which is the threshold which indicates a dangerous state), the priority is escalated (changed), and the alarm level is switched to the alarm of the high priority in a similar manner as described above.

In the case where the measured value of the SpO2 falls below 90% which is the lower limit value, the alarm of the medium priority is originally to be continued. In the invention, as described above, when the predetermined conditions are satisfied, the alarm level is switched to the alarm of the high priority. Therefore, attention is raised by increasing the volume of an audio alarm (auditory alarm), or increasing the blinking rate of a blinking alarm (visual alarm), as compared with that of the medium priority. As shown in Table 2, in the visual alarm, a color of an indicator light (a display color) may be changed depending on the priority of the alarm. In addition, as shown in Table 4, in the auditory alarm, a sound may be changed depending on the priority of the alarm.

Figure 3:
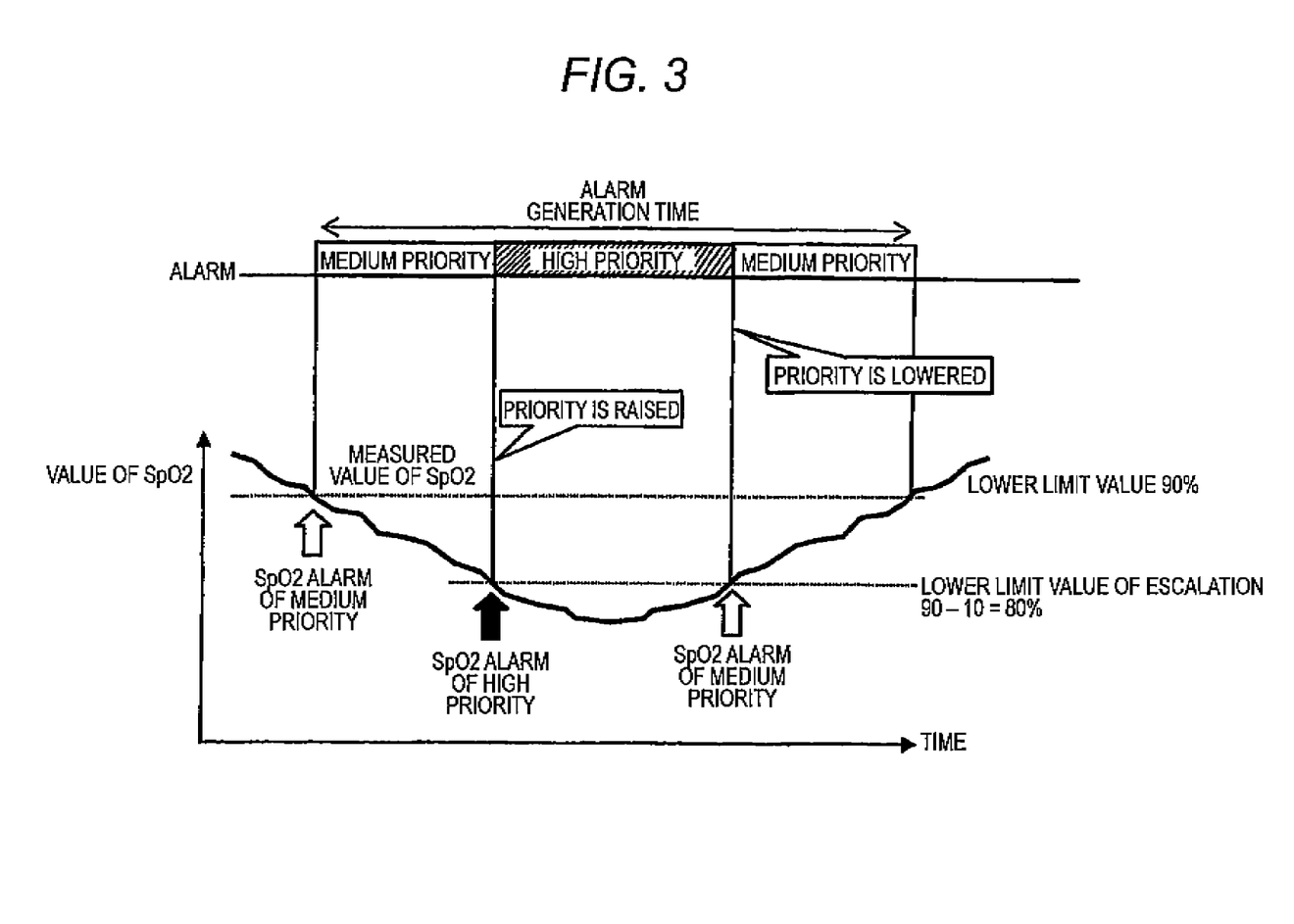
FIG. 3 is a view illustrating an example of an alarm priority change in the invention in the case where the state of the alarm deviates from predetermined conditions (an abnormal state).

In the case where, after the priority of the SpO2 alarm is changed to the high priority, the measured value of the SpO2 returns within the set value of the lower limit of the priority change, in other words, the measured value of the SpO2 exceeds the lower limit value of escalation (i.e., in the case where the patient moves from the dangerous state and returns to the abnormal state), as shown in FIG. 3, the priority of the SpO2 alarm is de-escalated (changed) to the alarm of the medium priority.

In FIG. 2, as illustrated, the priority change of the SpO2 alarm is set for example so that, as the reduction value from the lower limit value, −10% is set among OFF, −3%, −5%, and −10%, and, as the continuous time period of the reduction from the lower limit value, 5 m (minutes) is set among OFF, 1 m (minute), 2 m (minutes), 3 m (minutes), 5 m (minutes), and 10 m (minutes). These set values can be adequately changed.

Moreover, values other those in FIG. 2 can be set.

Although, in FIG. 2, the description is made by using the example of the alarm of SpO2, also the priority of an alarm with respect to a measured value other than SpO2, such as measured values of other biological signals, for example, measurements of the non-invasive blood pressure (NIBP), the electrocardiogram (ECG), and the respiration (RESP) can be changed.

In FIG. 2, the description is made by exemplifying the vital alarm of SpO2 which is a biological signal. Also with respect to a technical alarm which is generated by, for example, a failure of a biological signal measuring apparatus, checking of a probe, disabled pulse wave detection, an interruption of the radio wave (a wireless signal), or a failure of reception of a wireless signal, the priority of the alarm can be changed in the case where the predetermined conditions are satisfied.

Next, a setting example of the alarm priority change in the invention will be described with reference to Table 5.

abled analysis (noises) are configured so as to be set from candidates of OFF, 1 m, 2 m, 3 m, 5 m, and 10 m.

As the parameter and alarm item of a technical alarm, in the telemeter, the interruption of the radio wave (a wireless signal) is configured so as to be set from candidates of OFF, 1 m, 2 m, 3 m, 5 m, and 10 m.

Furthermore, in the telemeter, the battery replacement is configured so as to be set from candidates of OFF, 1 m, 10 m, 30 m, 60 m, and 120 m.

In Table 5, as alarm priorities before and after the priorities of vital and technical alarms are changed, a normal level and a level after the change of the priority are shown.

In Table 5, in SpO2, for example, the normal level (M) is changed to (H) after the priority is changed. As illustrated, the changed priority level can be set to be higher than the normal level. This is employed because an alarm of a higher level is generated so as to prevent the nurse or the like from overlooking the alarm.

Although, in Table 5, as examples of the alarm and the alarm item, two items, the SpO2 and the RESP are listed with respect to the vital alarm, and three items, the SpO2, the ECG, and the telemeter are listed with respect to the technical

TABLE 5

Conditions for generating escalation alarm

| | | | Setting of escalation alarm | | | | | | | |
|---|---|---|---|---|---|---|---|---|---|---|
| Kind | Parameter | Alarm item | Setting of generating conditions | | | | | | Normal level | Escalation level |
| Vital alarm | SpO2 | Reduction value from lower limit value | OFF | −3% | −5% | −10% | | | H/(M)/L | M (H) |
| | | | | | Continuous time period | | | | | |
| | | Continuous time period of reduction from lower limit value | OFF | 1 m | 2 m | 3 m | 5 m | 10 m | H/(M)/L | M (H) |
| | RESP | APNEA time | OFF | 20 s | 40 s | 60 s | | | H/(M)/L | M (H) |
| Technical alarm | SpO2 | Probe check | OFF | 1 m | 2 m | 3 m | 5 m | 10 m | M/(L) | (M) H |
| | | Disabled pulse wave detection | OFF | 1 m | 2 m | 3 m | 5 m | 10 m | M/(L) | (M) H |
| | ECG | Electrode check | OFF | 1 m | 2 m | 3 m | 5 m | 10 m | M/(L) | (M) H |
| | | Disabled analysis (noises) | OFF | 1 m | 2 m | 3 m | 5 m | 10 m | (M)/L | M (H) |
| | Telemeter | Interruption of radio wave (wireless signal) | OFF | 1 m | 2 m | 3 m | 5 m | 10 m | M/(L) | (M) H |
| | | Battery replacement | OFF | 1 m | 10 m | 30 m | 60 m | 120 m | M/(L) | (M) H Escalation level is set to only level higher than normal |

Table 5 shows an example of conditions for generating the alarm priority change in the invention.

In Table 5, as the parameter and alarm item of a vital alarm, in SpO2, the reduction value from the lower limit value is configured so as to be set from candidates of OFF, −3%, −5%, and −10%.

Furthermore, in the SpO2, the continuous time period of the reduction from the lower limit value is configured so as to be set from candidates of OFF, 1 m, 2 m, 3 m, 5 m, and 10 m.

As the parameter and alarm item of a vital alarm, in RESP (respiration), APNEA time is configured so as to be set from candidates of OFF, 20 s, 40 s, and 60 s.

As the parameter and alarm item of a technical alarm, in SpO2, the probe check and the disabled pulse wave detection are configured so as to be set from candidates of OFF, 1 m, 2 m, 3 m, 5 m, and 10 m.

As the parameter and alarm item of a technical alarm, in ECG (electrocardiogram), the electrode check and the disalarm, it is obvious that the concept of the invention can be applied also to vital and technical alarms other than the above-described ones.

In FIG. 2, the example of the priority change of the vital alarm of SpO2 which is a biological signal is described. However, technical alarms of a failure of a biological signal measuring apparatus, checking of a probe, disabled pulse wave detection, an interruption of the radio wave (a wireless signal), and the like are also important in the invention.

A generation of a technical alarm is performed in the case of a failure of a biological signal measuring apparatus itself, checking of a probe, disabled pulse wave detection, an interruption of the radio wave (a wireless signal), a failure of reception of a wireless signal, and the like. In the case where a failure of a biological signal measuring apparatus itself, checking of a probe, disabled pulse wave detection, an interruption of the radio wave (a wireless signal), a failure of reception of a wireless signal, and the like occurs, therefore, a technical alarm is generated.

A generation of a technical alarm means that a failure of a biological signal measuring apparatus itself, a state where checking of a probe, disabled pulse wave detection, an interruption of the radio wave (a wireless signal), a failure of reception of a wireless signal, or the like occurs. However, this is not directly related to a phenomenon in which an abnormality is caused in the biological signal of the patient. Therefore, there arises a problem in that, even when a technical alarm is continued, the nurse or the like overlooks the alarm.

During a period when a technical alarm is continued, the biological signal of the patient cannot be correctly measured. This may cause a serious abnormality of the biological signal of the patient to be overlooked.

In the invention, when a technical alarm is continued for a predetermined time period, therefore, the priority of the alarm is changed, and an alarm of a different priority is generated. Consequently, an escalation alarm attains an excellent effect in preventing a serious abnormality of the biological signal of the patient from being overlooked.

In a surgery room or the like from which the patient leaves, the measurement is not correctly performed, and hence a technical alarm (sometimes, a vital alarm) is often generated. In the invention, when a predetermined time period elapses, an alarm of higher priority may be sometimes announced. This situation is not desirable.

In the biological information monitoring apparatus, therefore, an inputting unit (not shown) through which the user directly operates the alarm controller may be disposed, and the user may operate the inputting unit, whereby an alarm of a high priority is de-escalated (changed) to that of a lower priority. According to the configuration, the above-described undesirable situation can be avoided.

The function of changing the alarm priority of the invention is provided in the biological information monitoring apparatus of the station type in which biological signals of a plurality of patients can be simultaneously monitored, as shown in FIG. 1. Also, the function of changing the alarm priority of the invention may be provided in a bedside biological information monitoring apparatus in which a patient in a medical ward or the like is individually monitored.

According to an aspect of the invention, in the case where, after a vital alarm that is output in abnormality of a biological signal, or a technical alarm that is output in abnormality of the biological information monitoring apparatus, a sensor, or the measurement environment is produced, the alarm is continued at the same priority, the priority of the alarm can be changed (for example, from the medium priority to the high priority) when the alarm state satisfies predetermined conditions.

Figure 4:
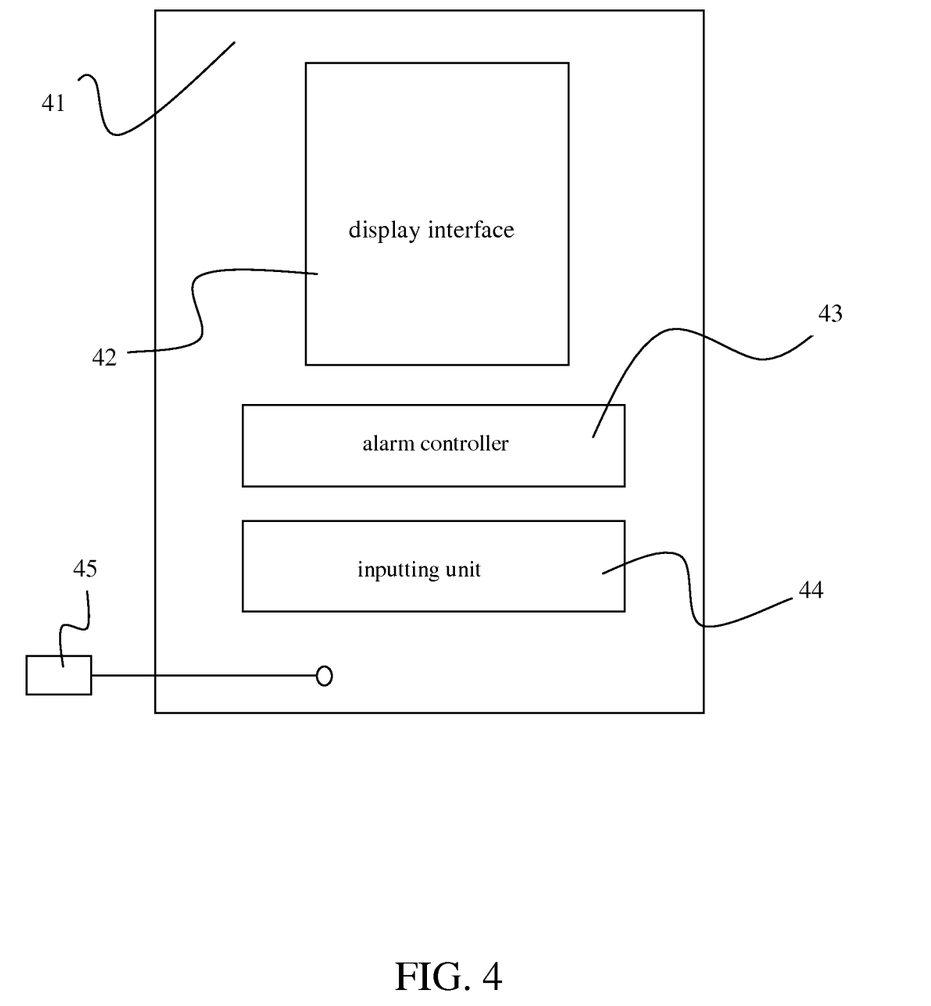
FIG. 4 is a schematic view illustrating an exemplary monitoring unit in accordance with principles of the disclosed subject matter.

FIG. 4 is a schematic view illustrating an exemplary monitoring unit in accordance with principles of the disclosed subject matter. A biological information monitoring apparatus 41 can be operable to measure biological information of a patient by detecting a biological signal of the patient via a sensor 45. The apparatus can be operable to output an alarm. The biological information monitoring apparatus 41 can include an alarm controller 43, an inputting unit 44, and a display interface 42.

What is claimed is:

1. A biological information monitoring apparatus operable to measure biological information of a patient by detecting at least one biological signal of the patient, and operable to output an alarm, the biological information monitoring apparatus comprising:

an alarm controller configured to change an outputted alarm from a first alarm of a first priority to a second alarm of a second priority, wherein, when a first condition is satisfied, the first alarm is output, and when a second condition is satisfied after the first alarm is output, the alarm controller changes the outputted alarm from the first alarm to the second alarm, wherein the outputted alarm is designated by the alarm controller as a vital alarm when outputted due to an abnormality in the detected at least one biological signal, when the detected at least one biological signal passes beyond a second condition threshold indicating a dangerous state, or the abnormality in the detected at least one biological signal is continued for a time period, the second condition is satisfied, and an alarm level, which corresponds to a priority selected from among at least the first priority and the second priority, is selected by a user for each kind of the at least one biological signal; and wherein the outputted alarm is designated by the alarm controller as a technical alarm when outputted due to an abnormality in at least one technical parameter associated with at least one of the biological information monitoring apparatus, a sensor for measuring the biological information, and a measurement environment of the biological information monitoring apparatus, when the abnormality in the technical parameter is continued for a time period, the second condition is satisfied, and an alarm level, which corresponds to a priority selected from among at least the first priority and the second priority, is selected by a user for each kind of the at least one technical parameter.

2. The biological information monitoring apparatus according to claim 1, further comprising:

an inputting unit, wherein after the alarm controller changes the outputted alarm from the first alarm to the second alarm, the user operates the inputting unit to change the outputted alarm from the second alarm to the first alarm.

3. The biological information monitoring apparatus according to claim 1, wherein the alarm controller further changes the outputted alarm from the second alarm to the first alarm when the second condition ceases to be satisfied, and the second condition ceases to be satisfied when the detected at least one biological signal no longer meets the second condition threshold.

4. The biological information monitoring apparatus according to claim 1, wherein the first condition is a condition that the detected at least one biological signal passes beyond a first condition threshold, and selection of the second condition threshold is based at least in part on the first condition threshold.

5. The biological information monitoring apparatus according to claim 1, wherein the second condition threshold is set from a plurality of candidate values.

6. The biological information monitoring apparatus according to claim 1, wherein the first alarm includes at least one of a first visual alarm and a first auditory alarm and the second alarm includes at least one of a second visual alarm and a second auditory alarm, a blinking rate of the second visual alarm when present is faster than a blinking rate of the first visual alarm when present, and a volume of the second auditory alarm when present is louder than a volume of the first auditory alarm when present.

7. The biological information monitoring apparatus according to claim 1, wherein the first alarm includes at least one of a first visual alarm and a first auditory alarm and the second alarm includes at least one of a second visual alarm and a second auditory alarm,
  a blinking rate of the second visual alarm when present is slower than a blinking rate of the first visual alarm when present, and
  a volume of the second auditory alarm when present is quieter than a volume of the first auditory alarm when present.

8. The biological information monitoring apparatus according to claim 1, wherein the first alarm includes at least one of a first visual alarm and a first auditory alarm and the second alarm includes at least one of a second visual alarm and a second auditory alarm,
  a display color of the second visual alarm when present is different from a display color of the first visual alarm when present, and
  a sound of the second auditory alarm when present is different from a sound of the first auditory alarm when present.

9. The biological information monitoring apparatus according to claim 1, wherein the outputted alarm is designated as a technical alarm when outputted due to an abnormality of (i) the biological information monitoring apparatus, (ii) a sensor for measuring the biological information that includes at least one of an oxygen saturation, a blood pressure, an electrocardiogram, and respiration, (iii) an interface between the sensor and the patient, or (iv) a communication of a wireless signal between components of the biological information monitoring apparatus.

10. The biological information monitoring apparatus according to claim 1, wherein the second priority is higher in priority than the first priority.

11. The biological information monitoring apparatus according to claim 1, wherein the first priority is higher in priority than the second priority.

12. The biological information monitoring apparatus according to claim 1, wherein the first alarm is output from a speaker, and the second alarm is output from the speaker.

13. The biological information monitoring apparatus according to claim 1, wherein the first priority and the second priority are different from each other in priority, and
  the first priority and the second priority are each one of a high priority, a medium priority and a low priority, which are alarm condition priorities in an alarm standard for a biological information apparatus.

14. The biological information monitoring apparatus according to claim 1, wherein the first priority and the second priority are preset based on degree of a risk resulting from the abnormality.

15. The biological information monitoring apparatus according to claim 1, wherein at least one of an auditory output or a visual output characterizing the second alarm changes as the dangerous state changes between a low priority state, a medium priority state and a high priority state.

16. The biological information monitoring apparatus according to claim 1, wherein the time period and the second condition threshold are each independently set from a plurality of candidate values.

17. A method of controlling an alarm outputted from a biological information monitoring apparatus operable to measure biological information of a patient by detecting at least one biological signal of the patient, the method comprising:
  outputting an alarm as a first alarm of a first priority when a first condition is satisfied, and
  changing the outputted alarm from the first alarm to a second alarm of a second priority when a second condition is satisfied after outputting the first alarm,
  wherein the outputted alarm is designated as a vital alarm when outputted due to an abnormality in the detected at least one biological signal,
  when the detected at least one biological signal passes beyond a second condition threshold indicating a dangerous state, or the abnormality in the detected at least one biological signal is continued for a time period, the second condition is satisfied, and
  an alarm level, which corresponds to a priority selected from among at least the first priority and the second priority, is selected by a user for each kind of the at least one biological signal; and
  wherein the outputted alarm is designated as a technical alarm when outputted due to an abnormality in a at least one technical parameter associated with at least one of the biological information monitoring apparatus, a sensor for measuring the biological information, and a measurement environment of the biological information monitoring apparatus,
  when the abnormality in the technical parameter is continued for a time period, the second condition is satisfied, and
  an alarm level, which corresponds to a priority selected from among at least the first priority and the second priority, is selected by a user for each kind of the at least one technical parameter.

18. The method according to claim 17, wherein the first alarm is output from a speaker, and the second alarm is output from the speaker.

19. The method according to claim 17, wherein the first priority and the second priority are different from each other in priority, and
  the first priority and the second priority are each one of a high priority, a medium priority and a low priority, which are alarm condition priorities in an alarm standard for a biological information apparatus.

20. The method according to claim 17, wherein the first priority and the second priority are preset based on degree of a risk resulting from the abnormality.

21. The method according to claim 17, wherein at least one of an auditory output or a visual output characterizing the second alarm changes as the dangerous state changes between a low priority state, a medium priority state and a high priority state.

22. The method according to claim 17, wherein the time period and the second condition threshold are each independently set from a plurality of candidate values.

* * * * *